United States Patent [19]

Casey et al.

[11] Patent Number: 4,678,658

[45] Date of Patent: Jul. 7, 1987

[54] AEROSOL GERMICIDE AND DYE

[75] Inventors: Irene Casey, Dept. 1013, P.O. Box 90020, Houston, Tex. 77290; Daniel Tusé, Fremont, Calif.

[73] Assignees: Larry Casey; Irene Casey, both of Houston, Tex.

[21] Appl. No.: 935,236

[22] Filed: Nov. 26, 1986

Related U.S. Application Data

[63] Continuation-in-part of Ser. No. 738,082, May 24, 1985, abandoned.

[51] Int. Cl.$^4$ .................. A61K 9/12; A61K 7/46; A61K 7/50; A01N 25/00
[52] U.S. Cl. .................... 424/7.1; 424/43; 424/45; 252/106; 252/408.1; 252/522 R
[58] Field of Search ............. 424/7.1, 43, 45; 252/106, 408.1, 522

[56] References Cited

U.S. PATENT DOCUMENTS

| | | |
|---|---|---|
| Re. 28,778 | 4/1976 | Winicov et al. ............ 252/106 |
| 1,696,762 | 12/1928 | Goodwin ............ 424/7.1 |
| 2,183,037 | 12/1939 | Bayliss et al. ............ 167/14 |
| 2,449,274 | 9/1948 | Broll ............ 167/33 |
| 2,496,270 | 2/1950 | Coler ............ 167/22 |
| 3,282,776 | 11/1966 | Kitzke ............ 167/39 |
| 3,287,214 | 11/1966 | Taylor et al. ............ 167/39 |
| 3,445,564 | 5/1969 | Kirschner ............ 424/45 |
| 3,624,219 | 11/1971 | Perlitsch ............ 424/7.1 |
| 3,791,983 | 2/1974 | Maierson ............ 252/305 |
| 3,832,459 | 8/1974 | Berkeley ............ 424/45 |
| 3,929,662 | 12/1975 | Boucher ............ 252/106 |
| 4,077,896 | 3/1978 | Bunegar et al. ............ 252/90 |
| 4,145,413 | 3/1979 | Usdin et al. ............ 424/63 |
| 4,201,764 | 5/1980 | French et al. ............ 424/45 |
| 4,321,277 | 3/1982 | Saurino ............ 424/329 |
| 4,568,534 | 2/1986 | Stier et al. ............ 424/7.1 |

OTHER PUBLICATIONS

Dainichiseika Chem. Abstr. (Columbus, Ohio, USA) 83 #81847v (1975).
Raychaudhuri Chem. Abstr. (Columbus, Ohio USA) 104 #31645J (1986).
Li Chem. Abstr. (Columbus, Ohio USA) 102 #197013K (1985).
Lamikanra Chem. Abstr. (Columbus, Ohio USA) 85 #14598t (1976).
Berthod Chem. Abstr. (Columbus, Ohio USA) 103 #27735a (1985).
Sanyo Chem. Abstr. (Columbus, Ohio USA) 102 #134012p (1984).
Fung Chem. Abstr. (Columbus, Ohio USA) 79 #111948r (1973).
Nippon Chem. Abstr. (Columbus, Ohio USA) 98 #55776m (1982).
Schimanski Chem. Abstr. (Columbus, Ohio USA) 94 #214398a (1981).
Kahn Chem. Abstr. (Columbus, Ohio USA) 88 #1544375B (1978).
Chiba Chem. Abstr. (Columbus, Ohio USA) 83 #133762K (1975).
Eiseman Chem. Abstr. (Columbus, Ohio USA) 64 -11867F (1966).
Soc. Anon. Chem. Abstr. (Columbus, Ohio USA) 26 #397 (1932).
Munden Chem. Abstr. (Columbus, Ohio USA) 88 #197457a (1978).

*Primary Examiner*—Shep K. Rose
*Attorney, Agent, or Firm*—Vaden, Eickenroht, Thompson & Boulware

[57] ABSTRACT

An aerosol spray for use in disinfecting a surface for personal use, such as a public restroom facility or telephone. The composition and delivery of the composition provides for the placement of a spray of disinfectant which includes a dye. The dye disappears as the spray effects the germicidal activity of the disinfectant. The composition is also rapidly drying, so that the dye disappears as well as the disinfecting composition leaving the surface dry.

7 Claims, No Drawings

AEROSOL GERMICIDE AND DYE

BACKGROUND OF THE INVENTION

This application is a continuation-in-part of U.S. Ser. No. 738,082 filed May 24, 1985, now abandoned, for "Germicide and Dye Composition and Method."

In an effort to protect the public from unsanitary surfaces in public restrooms, telephones and other surfaces which are contacted by the public a number of methods have been developed. Many people have an aversion to using public restroom facilities or other objects for personal use which have been used previously by others. With the increased concerns of *Herpes simplex* virus type 2 which is a persistent viral infection once contracted, the community has become increasingly cautious about exposure.

One of the more commonly available methods for protection is a disposable paper cover for the toilet facility. The paper covers do not contain a germicide and are not always available.

A spray germicide for sanitizing surfaces which is quick drying was disclosed in U.S. Pat. No. 3,445,564 to Kirscher. The patent discloses a spray and other alternative embodiments of a quick drying germicide. It does not disclose effectiveness against Herpes or the range of pathogens disclosed herein. Also, there is no disclosure of use of the disappearing dye which provides a visual assurance and confirmation of the area treated as well as an indicator of germicidal destruction.

The use of a dye in a bacteriacidal solution was disclosed in U.S. Pat. No. 2,449,274 to Broll. The use of the dye was in a bacteriacidal liquid to clean objects such as tableware. The solution would change color upon losing bacteriacidal strength. This was not a surface spray application with a dye indicator.

There are a number of applications for spray germicides such as the commercially available Lysol ® spray by Lehn and Fink Products Division of Sterling Drug, Inc. U.S. Pat. Nos. 3,282,776 and 4,201,764 are examples of surface or surface and space spray combinations. None of the patents or products include a dye which is used with the spray in any manner.

SUMMARY OF THE INVENTION

The purpose of this invention is to provide a germicidal composition with a disappearing dye which can be dispersed in a fine spray with the dye indicating the delivery of the germicide. Although the dye is added for color, it is thoroughly mixed and completely dispersed in the system so that a coating or fine layer of spray imparts the visual colored composition will also indicate an active germicidal coating or layer. The germicide is effective against *Herpes simplex* virus type 2 (HSV2) as well as bacteria such as *Staphylococcus aureus, Neisseria gonorrhoeae*, enteric bacteria *Escherichia coli* 011K58 (Pathogenic), *Shigella sonnei* and *Salmonella typhimurium*, and the yeast *Candida albicans*. The dye will be quite noticeable on lighter colored surfaces and therefore give a visual check as to the area disinfected. It is believed a novel spray with a dye included will enhance usage by the consumer.

Another aspect of the germicide is to provide one or move detergents as germicides. The detergents are surface active and attack the target pathogen but also, through the surface active qualities, causes the spray to spread effectively on the surface to be disinfected. The spreading aspect is especially helpful because the individual droplets dispensed from any type of spray device will spread to provide a more even layer before drying. In addition to the delivery of an effective germicide for a broad range of organisms with a dye, the composition is also quick drying.

The composition can be packaged in any type of airtight container such as an aerosol spray and can be made in a convenient size which can be carried in a purse or pocket. The composition can also be packaged in a larger size spray dispenser for multiple applications for home or commercial use.

DESCRIPTION OF THE PREFERRED EMBODIMENTS

The product is manufactured as a fluid which is packaged in an aerosol spray dispensing unit for personal or home use in the appropriate size of container. An aliphatic alcohol with high volatility is used as the primary component by volume. The alcohol has bacteriacidal characteristics and allows for the rapid drying of the layer of disinfectant sprayed on the surface. For use in public restrooms a rapidly drying composition would be most desirable for use. Due to cost and availability, isopropanol is utilized in the examples although other quick-drying alcohols could be substituted. The isopropanol can be mixed with an amount of water and the examples show about a 70% isopropanol mixture with 30% water.

Disinfecting surfactant-detergent compounds are also used in the fluid composition. Surfactants are effective germicides and attack the membranes of the organisms. Also, the surfactants are surface active reducing surface tension. This phenomena causes the spreading over the surface of the disinfecting composition providing a more effective distribution of the germicide spray on the surface. It is thought that the surfactant has two characteristics which contribute to this invention. Those being germicidal activity including effectiveness over a wide range of organisms including bacteria, virus and yeast and providing a reduction of the surface tension of the composition to achieve effective spread and distribution if the germicide on the surface to be disinfected. Two different types of surfactants were tested separately and in combination for efficacy. It was found that both sodium dodecyl sulfate and octyl phenoxy polyethoxyethanol are effective germicide-surfactants. There are other compounds which have the properties of germicide-surfactants, and this invention is not limited to those compounds shown in the examples.

The composition contains a dye which is dissolved and dispersed in the composition. In the examples, the dye selected is a pH indicator blue dye which is colored at alkaline pH and upon neutralization becomes colorless. The blue dye was chosen for the examples because of a clean association by the public with the blue color. Any other dye color could be used which would be acceptable for a particular use. Other indicators which have the similar pH sensitivity can be used as shown, for instance in the Table of "Indicators for Volumetric Work and pH Determination" in the *Merck Index* 10th Ed. (1983).

The composition of the examples has the pH adjusted with the addition of an alkali such as sodium hydroxide so that the blue color is deep and noticeable when applied, but losing color upon use. The pH sensitive dye was chosen for use by the public because the delivery of the alkaline composition in the environment causes the color to change in a short period of time. The color change is probably due to the neutralization of the composition from $CO_2$ in the air and the surface on which it is sprayed. The alkalinity of the material is adjusted carefully so that the neutralization of the composition can produce a visual change from blue to clear within a short period of time. During the neutralization of the composition and visible change of color, the alcohol surfactant germicide is producing an effective kill on organisms present. The disappearance of the color, the killing of the organisms, and the drying of the germicide occur in rapid sequence leaving a dry, germ-free surface for personal use.

It is also found that this composition does not leave a film after drying so that the surface is not tacky and undesirable for personal use. Also, the composition does not have an objectionable odor as found in phenolic type germicides. Perfume additives may be used to provide a fragrance if desired but are not necessary to mask the odor of the germicidal composition.

There is a factor of the necessity of an airtight container for a pH sensitive dye. If ambient air is allowed to penetrate into the container, the liquid may be neutralized and the color will disappear. Also, the highly volatile alcohol will escape if the container is not sealed. The disappearance of the color will not affect the strength of the germicide detergent which have a long shelf life.

For personal use a small aerosol container which delivers a fine spray is a practical packaging for the composition. For commercial packaging a hydrocarbon propellant is preferable to meet environmental quality standards. For testing a fluorocarbon propellant of the Freon type was used. A propellant system to deliver a fine spray is preferable because it will deliver a fine, rapidly spreading layer which will dry quickly. Atomizers or other devices which deliver a denser spray may necessitate the wiping of the composition with toilet paper or other wipe before use because of a longer evaporation time for a dense spray. Another preparation of the invention can be the saturation of a woven wipe which is sealed in a foil or other airtight packaging. The packet would be torn open for a one-time usage of the wipe delivering the dye colored germicide to the surface. The rubbing of the wipe on the surface will promote evaporation of the composition.

EXAMPLE I

A sample of the germicidal composition was prepared by adding 400 mg of sodium dodecyl sulfate (SDS) and 400 of octyl phenoxy polyethoxyethanol marketed as Triton X-100 a product of Sigma Chemical Company to 100 ml of 70% by volume isopropanol. 100 mg of blue dye thymophthalein was added. The pH was adjusted with 0.05 ml of 12N NaOH which produces a deep blue colored liquid when keep air tight. This also gave a pH of 12.53 to the liquid. When the composition is allowed to stand exposed to air it becomes colorless and the pH drops to 8.8. Tests were done on adjusting the pH with the blue dye thymophthalein and it was found that the dark blue color is present at about 11.27 pH. A lighter blue is present at 11.01 pH and the liquid is clear at 10.95 pH and lower. An initial dark blue was used in Example 1 to produce a colored spray. However, the NaOH added was not excessive to prevent bleaching when the composition is exposed as a spray or thin coating on a surface in the normal atmosphere.

This composition was tested for germicide effectiveness against *Herpes simplex* virus type 2 (HSV2), *Neisseria gonorrhoeae, Staphylococcus aureus, Escherichia coli* 011K58, *Shigella sonnei, Salmonella typhimurium,* and *Candida albicans*. The composition was sprayed and dropped on pathogen suspensions to test efficacy and dye color disappearance.

In both the spray and drop tests 0.1 milliliters (ml) of test pathogenic organisms containing approximately $1 \times 10^7$ organisms were placed on the surface of a sterile plastic Petri dish. In the drop test 0.1 ml of the composition of Example I was added by pipette to the pathogen suspension in the Petri dish. The pathogen suspension and drop of Example I were mixed and allowed to stand for twenty seconds. The blue color would disappear before the twenty seconds elapsed. At the end of twenty seconds the Petri plate was tilted and 0.1 ml of the test sample was removed. In the spray test the composition of Example I was placed in an aerosol spray with a fluorocarbon propellant. The 0.1 ml of the pathogenic organism suspension in the Petri plate was sprayed for two seconds with Example I. It was determined that between 0.6 and 0.9 ml of liquid was delivered in the two second spray. The spray spreads quite noticeably over the Petri plate and the blue color disappears in a short time. The spray was allowed to mix on the Petri plate for twenty seconds. After twenty seconds the Petri plate was tilted and 0.1 ml of the sample was removed for testing.

The test samples removed from the drop and spray tests were diluted and plated on agar medium (casman media for *S. typhimurium, S. sonnei* and *E. coli;* chocolate agar supplemented with factor XV for *N. gonorrhoeae,* and sheep blood agar for *S. aureus* and *C. albicans*). HSV2 was added to the first wells of a 96-well sterile microtiter tissue culture plate, serially diluted and cultured with VERO monkey kidney cells for five days. Phosphate buffered saline was used as a diluent for all organisms except *N. gonorrhoeae* and HSV2; phosphate buffered saline (PBS) containing 0.5% gelatin was used as a diluent for the *N. gonorrhoeae* and minimal essential medium supplemented with 5% fetal calf serum and antibiotics was used for the HSV2. Each test included a control (pathogenic organism+diluent) and a quantitative titration of the pathogen to determine the actual number of organisms in each test suspension. All Petri and tissue culture plates were incubated in 37° C. (5% $CO_2$) incubators.

All Petri plates were observed the morning after plating for colony forming units (CFU) and the number of organisms present in the test suspensions were calculated. The tissue culture plates containing VERO cells were observed daily for virus specific cytopathic effects (CPE). At the end of five days the last well in each series of dilutions showing CPE was recorded and the tilter of virus in the original test suspensions calculated. Each assay involving HSV2 had a tissue culture control (VERO cells+media only) and a virus control (VERO cells+HSV2 and no germicide).

The results of the cidal activity of Example I are shown in Table 1.

TABLE 1

The Microcidal Activity of Example I Against Various Pathogens.

| Pathogen | No. of tests | Mean Percent killing | Range | Comments |
|---|---|---|---|---|
| S. aureus | 6 | >99* | 99–99.9 | Similar killing by drop or spray. |
| C. albicans | 6 | >99 | 99–99.9 | Similar killing by drop or spray. |
| N. gonorrhoeae | 5 | >99 | 99–99.9 | Similar killing by drop or spray. |
| E. coli 011K58 | 3 | >99 | 99–99.9 | Similar killing by drop or spray. |
| S. sonnei | 3 | >99 | 99–99.9 | Similar killing by drop or spray. |
| S. typhimurium | 3 | >99 | 99–99.9 | Similar killing by drop or spray. |
| HSV2 | 5 | 99 | 99–99 | Similar killing by drop or spray; may be > than 99% killing but toxicity of Example I to VERO cells made lower dilutions unreadable. |

*Percent killing was determined by dividing the total number of viable organisms in suspensions exposed to Example I by the total number of viable organisms in suspensions exposed to phosphate buffered saline and multiplying by 100.

Example I was compared to Lysol for strength of killing the organisms HSV2, S. aureaus, N. gonorrhoeae. E. coli 011K58, S. typhimurium, S. sonnei and C. albicans, the complete range of pathogens tested previously. The test was conducted for spray delivery. Example I was found to compare with the percentage kill equivalent to Lysol in a side by side test.

The composition was diluted to determine efficacy. Distilled water was chosen as the dilutant because PBS caused a cloudy liquid and additional alcohol would affect germicidal properties. There was a noticeable decrease in surface tension reduction decreasing the spreading of the composition with a tenfold dilution with water. After a 100-fold dilution with water, no reduction in surface tension was seen. The killing effect of the dilutions of this example are shown in Table 2.

TABLE 2

The Microcidal Effect of Different Dilutions of Example I Against Various Pathogens.

| Pathogen | No. of tests | Percent of killing at dilution | | | |
|---|---|---|---|---|---|
| | | 0 | 10-fold | 100-fold | 1000-fold |
| S. aureus | 3 | >99/>99/>99* | 37/90/99 | 8/54/90 | 20/75/ND** |
| C. albicans | 3 | >99/>99/>99 | 40/13/95 | 0/53/25 | 0/0/ND |
| N. gonorrhoeae | 3 | >99/>99/>99 | >99/72/90 | 0/74/92 | 15/0/79 |
| HSV2 | 2 | 99/99 | 99/99 | 0/7 | 0/7 |

*Results of replicate experiments are separated by slant (/) bars.
**ND = not done.

EXAMPLE II

Another embodiment of the composition can be made using SDS as the only surfactant-germicide. The composition was prepared as described in Example I omitting the addition of Triton X-100 and using 400 mg of SDS as the only surfactant-germicide. Testing the cidal activity of Example II on the organisms listed in Table 3 below was carried out as previously outlined in Example I.

TABLE 3

The Microcidal Effect of Example II.

| Organism | No. of Tests | % Killings | |
|---|---|---|---|
| | | Spray | Drop |
| HSV2 | 2 | 99 | 99 |
| N. gonorrhoeae | 2 | >99 | >99 |
| S. aureas | 2 | >99 | >99 |
| C. albicans | 2 | >99 | >99 |

EXAMPLE III

An alternate embodiment of the composition can be made using Triton X-100 as the only surfactant-germicide. The composition was prepared as described in Example I omitting SDS and adding 400 mg of Triton X-100 as the only surfactant-germicide. Testing on the organisms listed in Table 4 below was carried as previously outlined in Example I.

TABLE 4

The Microcidal Effect of Example III.

| Example Organism | No. of Tests | % Killings | |
|---|---|---|---|
| | | Spray | Drop |
| HSV2 | 2 | 99 | 99 |
| N. gonorrheae | 3 | >99 | >99 |
| S. aureas | 3 | >99 | >99 |
| C. albicans | 3 | >99 | >99 |

EXAMPLE IV

A formula for use with a hydrocarbon propellant is shown in the following Table 5.

TABLE 5

| Biocide and Hydrocarbon Propellant | |
|---|---|
| Ingredient | Weight % |
| Isopropanol | 51.62 |
| Dionized Water | 27.52 |
| Triton X-100 | 0.38 |
| TEA-Lauryl Sulfate | 0.38 |
| Thymolphthalein | 0.10 |
| Aeropin-70 Propellant | 20.00 |

In this example, Triethanol Amine Lauryl Sulfate was used. The Composition is adjusted to pH 11.5 with 10% NaOH. The Aeropin-70 is a hydrocarbon propellant of the following composition in Table 6.

TABLE 6

| | Hydrocarbon Propellant | | |
|---|---|---|---|
| | Liquid Volume % | Molecular % | Weight % |
| Propane | 51.05 | 54.79 | 47.92 |
| Isobutane | 19.81 | 17.84 | 20.61 |

TABLE 6-continued

| Hydrocarbon Propellant | | |
|---|---|---|
| Liquid Volume % | Molecular % | Weight % |
| N—butane 29.14 | 27.32 | 31.47 |

The propellant system used can be any environmentally acceptable spray that disperses the biocide in a fine layer.

As seen from the result of testing on a wide range of pathogens, a composition containing one or more surfactant-germicide provides very effective killing strength used as a drop or spray. Various other surfactants could be substituted as the surfactant-germicide and it is not the intent of the invention to limit the compounds used.

What is claimed is:

1. A biocide aerosol spray dispensing unit for disinfecting a surface with a fine spray consisting essentially of
   a fluid biocide;
   a sufficiently airtight container for said fluid biocide;
   said fluid biocide including a lower alkyl alcohol having 1 to 4 carbon atoms, an effective amount of a disinfecting surfactant, a pH sensitive dye, and alkali means for adjusting the pH of the fluid to produce a color in the liquid in the dye so that upon neutralization the dye loses color; and
   a propellant system to disperse a fine spray of said biocide on the surface to be disinfected.

2. A biocide aerosol of claim 1 wherein said pH sensitive dye is an indicator which is colored in the alkali state and loses color when dispersed as a fine spray upon oxidation in the atmosphere.

3. A biocide aerosol of claim 1 wherein said alcohol is mixed with water up to about 30% of water.

4. A biocide aerosol of claim 1 wherein said alcohol is isopropanol.

5. A biocide aerosol of claim 1 wherein said disinfecting surfactant is selected from the group of sodium dodecyl sulfate, octyl phenoxy polyethoxyethanol, triethanol amine lauryl sulfate and mixtures thereof.

6. A biocide aerosol of claim 1 wherein said propellant is selected from a fluorocarbon or hydrocarbon propellant.

7. A biocide aerosol of claim 1 with a fragrance additive.

* * * * *

UNITED STATES PATENT AND TRADEMARK OFFICE
CERTIFICATE OF CORRECTION

PATENT NO. : 4,678,658
DATED : July 7, 1987
INVENTOR(S) : Irene Casey and Daniel Tuse It is certified that error appears in the above-identified patent and that said Letters Patent is hereby corrected as shown below:

On the title page, Item [75] "Inventors:" should read:

Irene Casey, P. O. Box 690566
    Houston, TX 77269-0566, Daniel
    Tuse, Fremont, Calif.

Signed and Sealed this

Fifteenth Day of January, 1991

Attest:

HARRY F. MANBECK, JR.

*Attesting Officer*      *Commissioner of Patents and Trademarks*